(12) United States Patent
Howard et al.

(10) Patent No.: US 7,007,306 B2
(45) Date of Patent: Mar. 7, 2006

(54) FACE SHIELD ASSEMBLY

(75) Inventors: Jeremy C. Howard, Little Compton, RI (US); Luke W. Michas, Westerly, RI (US); Richard W. Canavan, Woodstock, CT (US); Raymond Curci, Smithfield, RI (US); Laurent Froissard, Cranston, RI (US); Philip M. Johnson, Charlton, MA (US); Erica L. Osley, Coventry, RI (US)

(73) Assignee: Bacou-Dalloz Eye & Face Protection, Inc., Smithfield, RI (US)

( * ) Notice: Subject to any disclaimer, the term of this patent is extended or adjusted under 35 U.S.C. 154(b) by 0 days.

(21) Appl. No.: 10/700,940

(22) Filed: Nov. 4, 2003

(65) Prior Publication Data
US 2005/0091732 A1 May 5, 2005

(51) Int. Cl.
*A42B 1/00* (2006.01)

(52) U.S. Cl. .................................... 2/9; 2/424
(58) Field of Classification Search ............... 2/416, 2/420, 424, 10, 427, 429, 452, 8, 453, 9; 128/201.24, 206.23
See application file for complete search history.

(56) References Cited

U.S. PATENT DOCUMENTS

| | | | |
|---|---|---|---|
| 2,326,376 A * | 8/1943 | Markgraf, Jr. et al. ............. 2/8 |
| 2,631,287 A * | 3/1953 | Malcom, Jr. ..................... 2/9 |
| 3,075,201 A * | 1/1963 | Lindblom ........................ 2/8 |
| 3,212,101 A * | 10/1965 | Benner .......................... 2/8 |
| 3,259,908 A | 7/1966 | Simpson et al. |
| 3,789,428 A | 2/1974 | Martin |
| 4,076,373 A | 2/1978 | Moretti |
| 4,097,929 A | 7/1978 | Lowe et al. |
| 4,101,980 A | 7/1978 | Stepan et al. |
| 4,462,119 A | 7/1984 | Rudd |
| 4,507,809 A | 4/1985 | Stepan |
| 4,536,892 A * | 8/1985 | Brinkhoff et al. ............... 2/424 |
| 4,542,538 A | 9/1985 | Moretti et al. |
| 4,748,695 A | 6/1988 | Shigematsu et al. |
| 4,748,697 A * | 6/1988 | Hodnett ......................... 2/438 |
| 4,888,831 A | 12/1989 | Oleson |
| D320,870 S | 10/1991 | Asbury et al. |
| 5,077,836 A | 1/1992 | Idoff et al. |
| 5,410,757 A | 5/1995 | Vienamo et al. |
| 5,571,217 A * | 11/1996 | Del Bon et al. .................. 2/9 |
| 5,793,449 A | 8/1998 | Lagerwall |
| D416,649 S | 11/1999 | Burns et al. |
| 6,102,033 A | 8/2000 | Baribeau et al. |
| 6,260,197 B1 * | 7/2001 | Hoogewind ....................... 2/8 |
| 6,317,895 B1 | 11/2001 | Erth et al. |

* cited by examiner

Primary Examiner—Rodney M. Lindsey
(74) Attorney, Agent, or Firm—Salter & Michaelson

(57) ABSTRACT

A face shield assembly including a frame and a removable protective element supported by the frame is disclosed herein. The protective element is removably supported in an opening of the frame by a channel, without the use of fasteners. Because the face shield lacks fasteners, it is easy to remove and replace, even with the use of gloves. In one embodiment, the frame is molded as a single, unitary member and includes an upper detent, a lower detent and a channel formed between a lip and the frame that receives an edge of the protective element in order to hold the protective element within the frame. In another embodiment, the frame is pivotally supported on a support structure such that the frame can be moved between an upper (out of use) and a lower (in use) position, and may further include an adjustable mounting member so that the frame can be selectively spaced relative to the user's head.

25 Claims, 20 Drawing Sheets

FACE SHIELD ASSEMBLY

TECHNICAL FIELD

The present disclosure is directed to a shield to protect the face of a user, and, more particularly to an improved face shield assembly that includes a frame for supporting a protective element without the use of fasteners or the like, which easily and comfortably shields the face of the user, and which provides good visibility.

BACKGROUND

The use of face shields to protect a user's eyes and face from various occupational hazards is well known in the art. Face shields are used in numerous professions as protective equipment including, for example, in the chemical, medical, construction, and manufacturing fields. Because face shields are utilized in a wide variety of industries, the requirements for protection can vary from industry to industry. While one industry may require protection against hazardous chemicals, another may require protection against flying debris, still another may require protection against extreme temperatures or light, and others may require protection against undesirable physical contact with body fluids. Thus, developing a face shield that can be utilized for a variety of applications can be a challenging task. In addition, some industries require the use of supplemental protection equipment, such as goggles, respirators and hoods with face shields. In these industries, the face shield must be able to accommodate such accessories. Finally, because people's faces vary widely in size and shape, face shields should be capable of providing protection for a wide variety of users.

Face shields are typically supported on a user's head by a headband, visor, or helmet, with the face shield attached such that it is positioned in front of the user's face during operation. Many face shields can pivot from a lowered position (during use) to an upward position (when not in use). It is common for face shields to be worn for extended periods of time. As such, it is important that the face shield be comfortable to wear. In addition, the face shield should provide adequate protection while not limiting visibility. Thus, proper fit is important because it aids in both comfort and protection. The lens of most face shields come into contact with various types of debris, all of which can damage the lens, especially over time. Thus, it is also advantageous if the lens can be replaced, as needed, during use. Because many workers use other protection gear, for example gloves, it is also desirable that the removal and insertion of the lens be readily achieved without compromising the security of the lens during use.

While a variety of face shields exist today, there is a continued need in the art for a face shield that has lasting comfort, does not obscure the user's view, provides the desired protection in a variety of applications and for a variety of users, is simple to use, and which provides for quick and easy replacement of the lens during use.

SUMMARY

It is therefore an object of the face shield assembly disclosed herein to provide a face shield which is comfortable to wear over time, does not unacceptably obscure the user's view, provides the desired protection to the user, is simple to use, and which provides for quick and easy replacement of the lens by the user.

There is provided herein a face shield assembly including a frame and a removable protective element supported by the frame. The protective element is removably supported in an opening of the frame by a channel, without the use of fasteners. Because the face shield lacks fasteners, it is easy to remove and replace, even with the use of gloves. In one embodiment, the frame is molded as a single, unitary member and includes an upper detent, a lower detent and a channel formed between a lip and the frame, the channel receiving an edge of the protective element in order to hold the protective element within the frame. In another embodiment, the frame is pivotally supported on a support structure such that the frame can be moved between an upper (out of use) and a lower (in use) position, and may further include an adjustable mounting member so that the frame can be selectively spaced relative to the user's head.

BRIEF DESCRIPTION OF THE DRAWINGS

It should be understood that the drawings are provided for the purpose of illustration only and are not intended to define the limits of the invention. The foregoing and other objects and advantages of the embodiments described herein will become apparent with reference to the following detailed description when taken in conjunction with the accompanying drawings in which.

DETAILED DESCRIPTION OF THE ILLUSTRATIVE EMBODIMENTS

Figure 1:
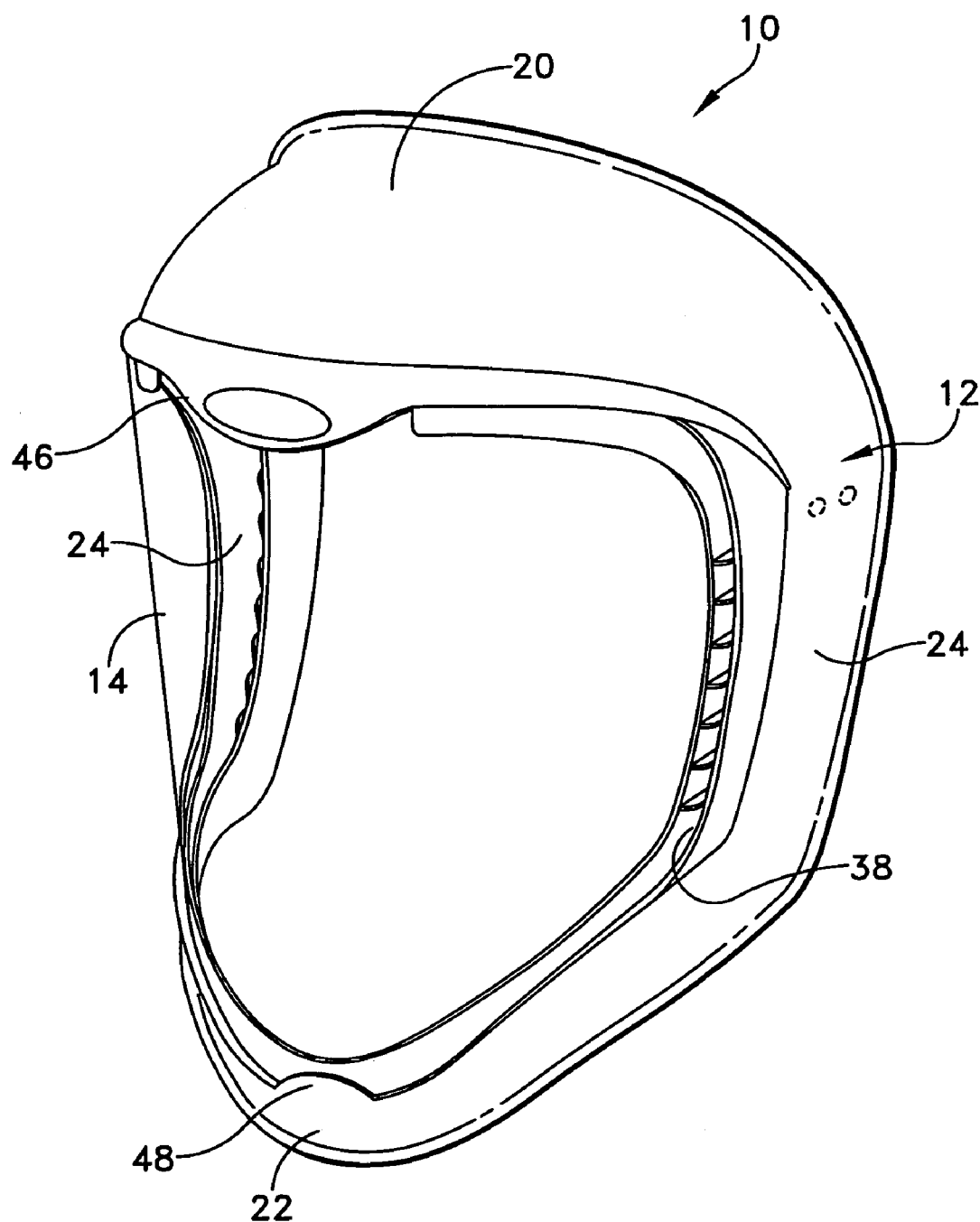
FIG. 1 is a front perspective view of a face shield assembly in accordance with the present invention including a protective element supported within a frame.
Figure 2:
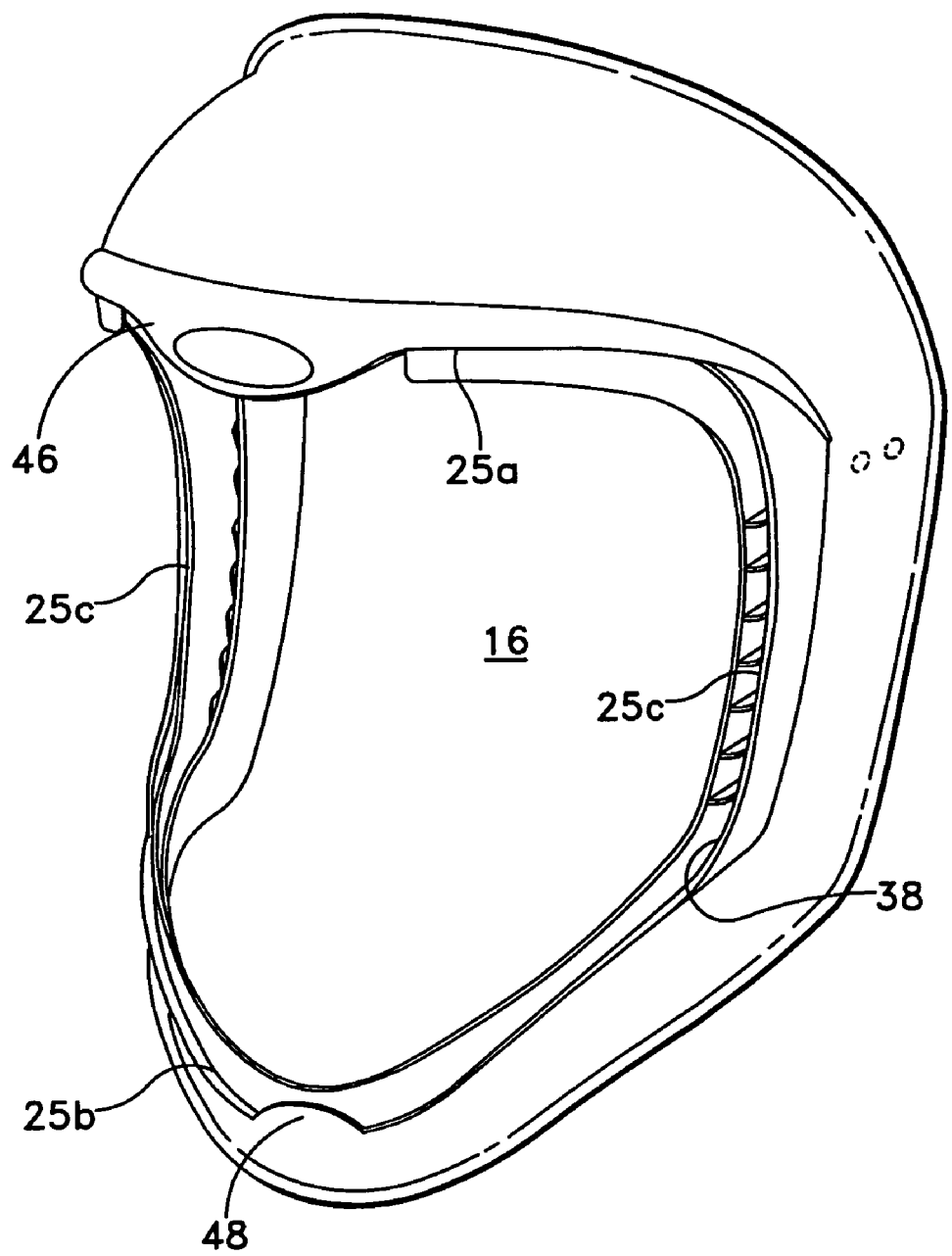
FIG. 2 is a front perspective view of the face shield assembly of FIG. 1 without the protective element.

A face shield assembly for protecting a user's eyes and face is illustrated in FIGS. 1–22. The face shield assembly 10 includes a frame 12 and a protective element 14 that is removably supported in an opening 16 of the frame. The assembly may also include a head worn support structure 18 for supporting the frame in an upper and lower position, as described in greater detail below.

Figure 19:
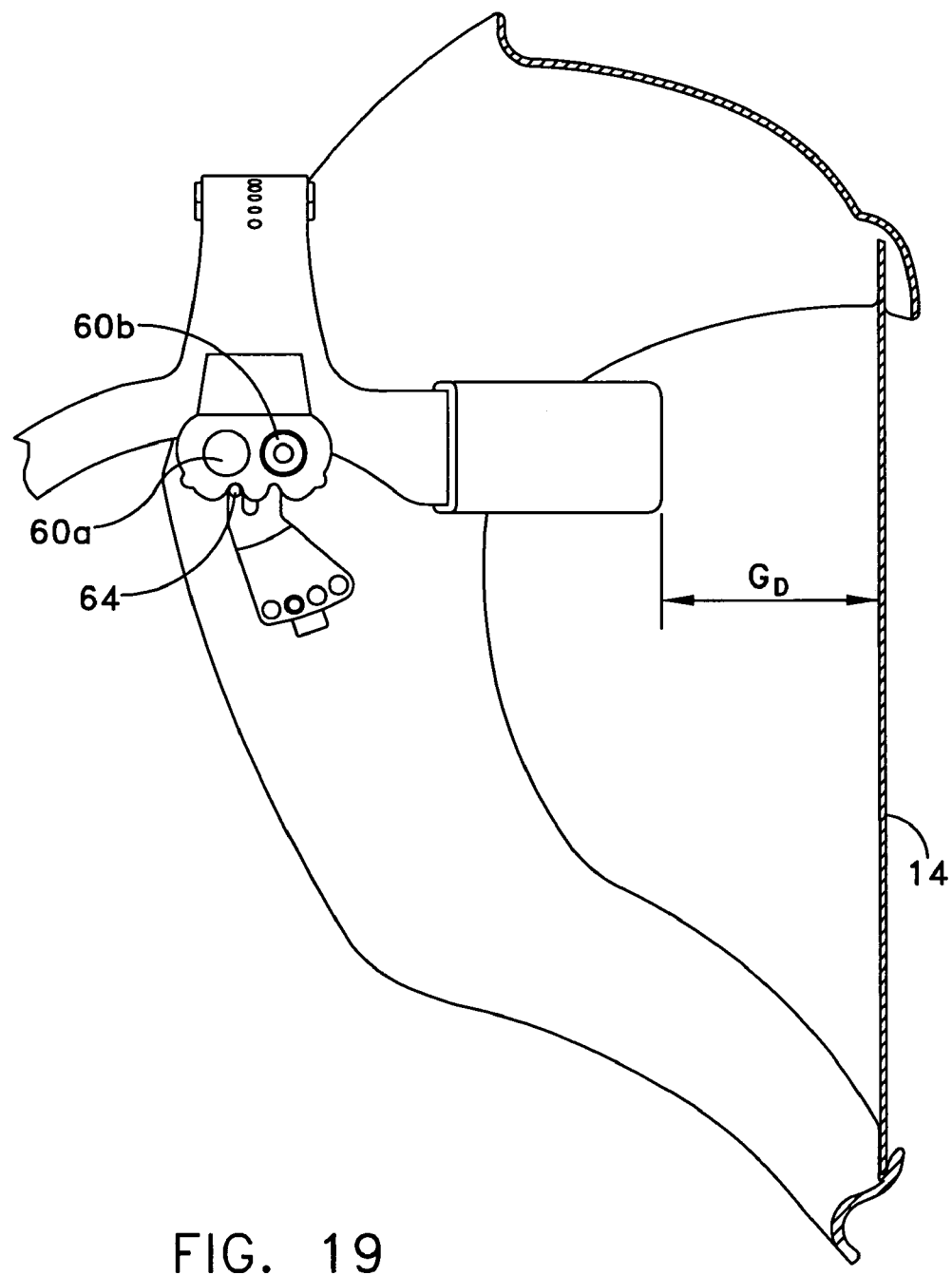
FIG. 19 is a side view illustrating the face shield mounted to a distal mounting hole of the support structure.
Figure 20:
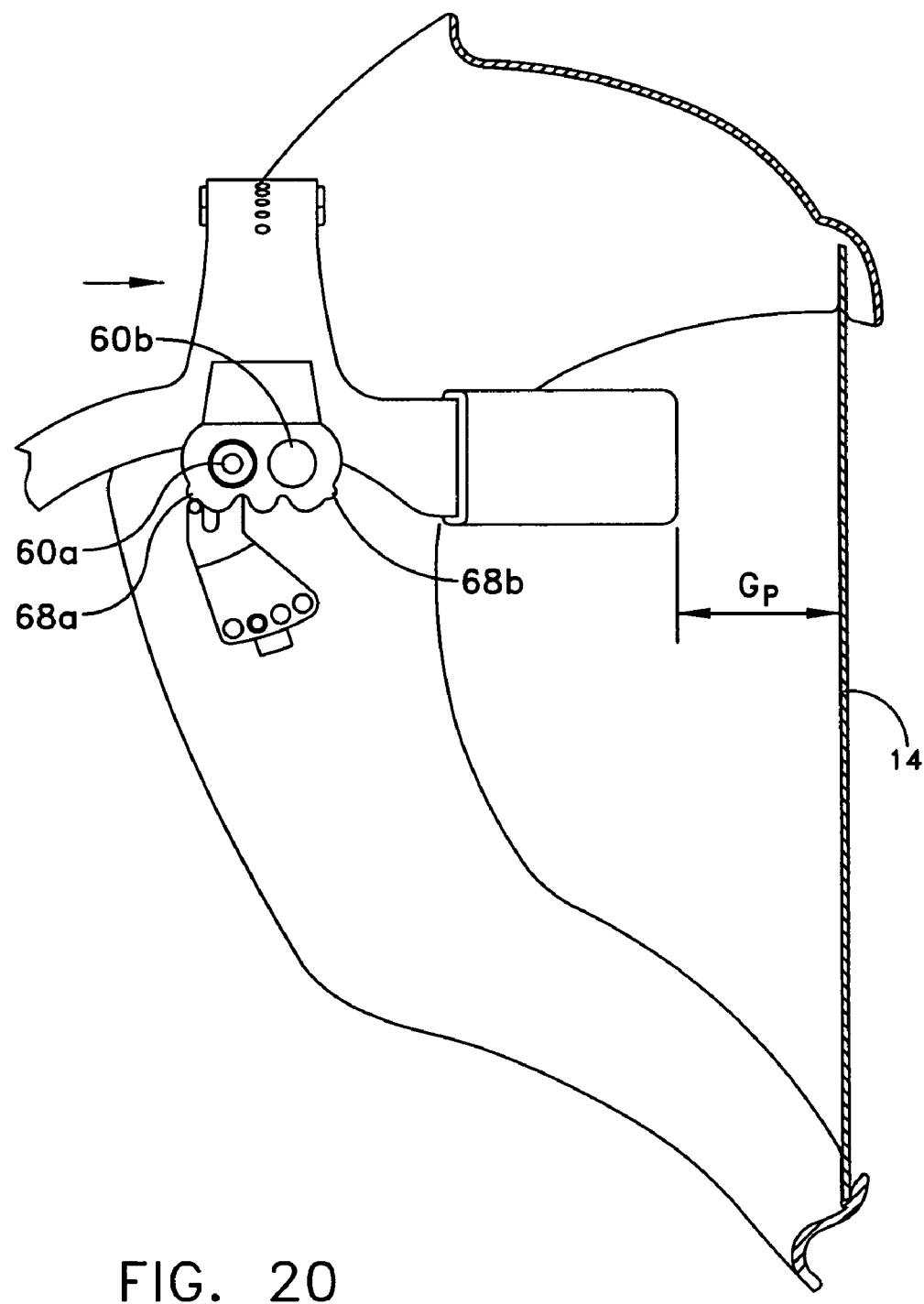
FIG. 20 is a side view illustrating the face shield mounted to a proximal mounting hole of the support structure in the lowered position.
Figure 21:
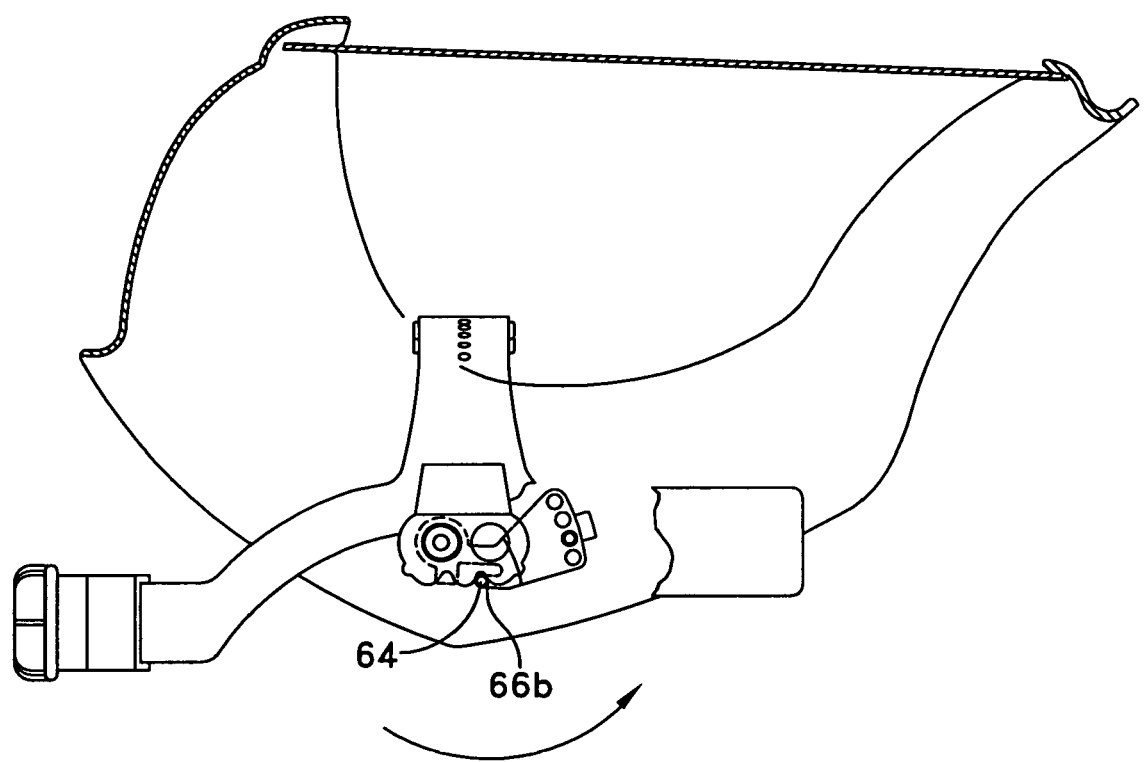
FIG. 21 is a side view illustrating the face shield mounted to a proximal mounting hole of the support structure in the upper position.
Figure 22:
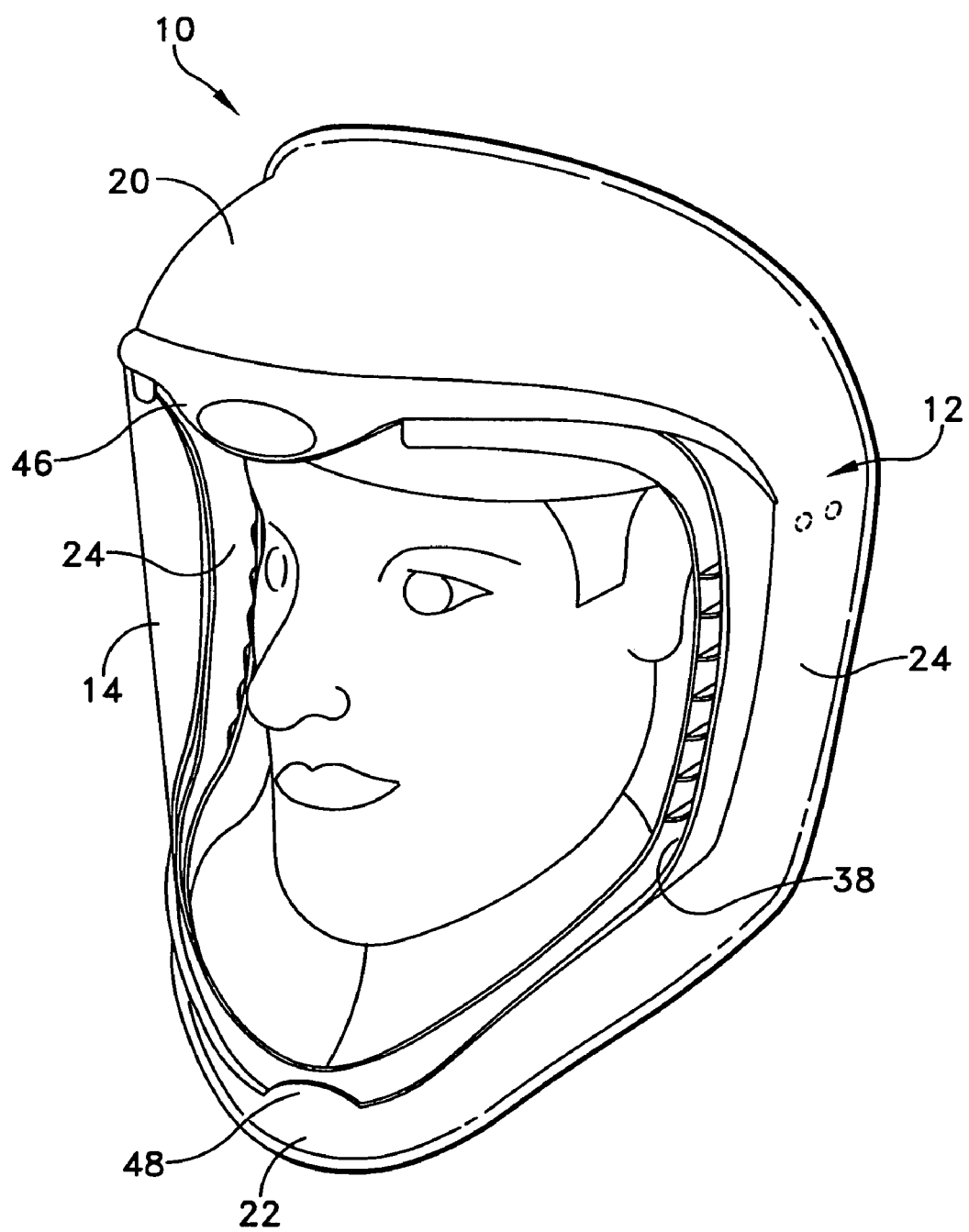
FIG. 22 is a perspective view of the face shield assembly on a user.

The frame 12 preferably includes a top portion 20, a bottom portion 22, and side portions 24. In use, the top portion rests adjacent the forehead and top of the head of a user, while the bottom portion lies adjacent the jaw of the user, and the side portions are disposed adjacent the ears of the user (FIG. 19). In the present embodiment, the top, bottom and side portions are preferably fabricated as a single, unitary member out of a lightweight material, for example polycarbonate or nylon although other lightweight materials may be utilized, as would be known to those of skill in the art. An opening 16 that is bounded by an inner edge 25a, 25b and 25c of the top, bottom and side portions, respectively, of the frame is also provided. The opening 16 is sized to receive the protective element 14 and preferably extends from a centerline of the face shield toward the edges of the face shield, so that the frame 12 does not obstruct the peripheral vision of the user.

The protective element 14 may be a lens made of a substantially transparent material, may be a mesh having very fine openings, or may be made of any other suitable material known in the art. The protective element 14 is preferably formed as a single, unitary member having a shape defined by an outer edge 28 (FIG. 3), which is preferably continuous. Because the protective element 14 is supported within the frame 12 without the use of fasteners, there is no need for any openings for receiving fasteners in the protective element 14.

Figure 3:
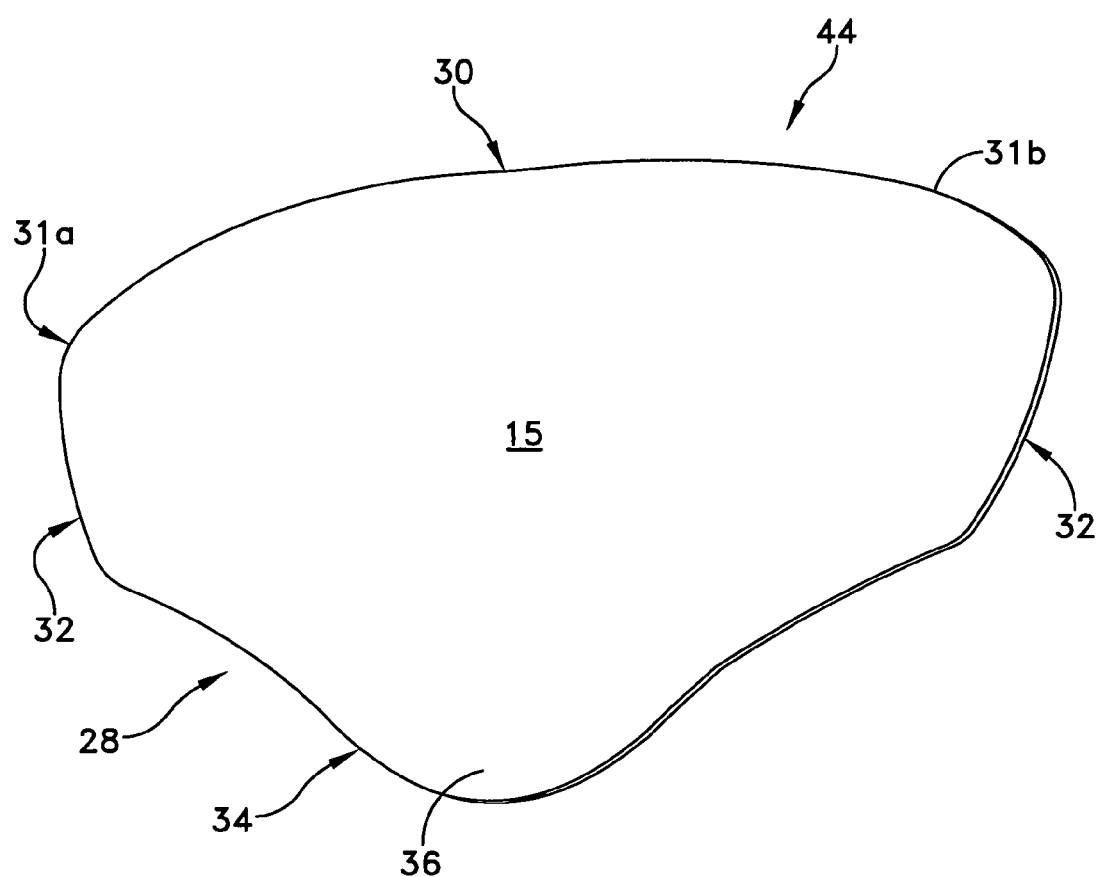
FIG. 3 is a perspective view of one embodiment of the protective element of FIG. 1.
Figure 4A:
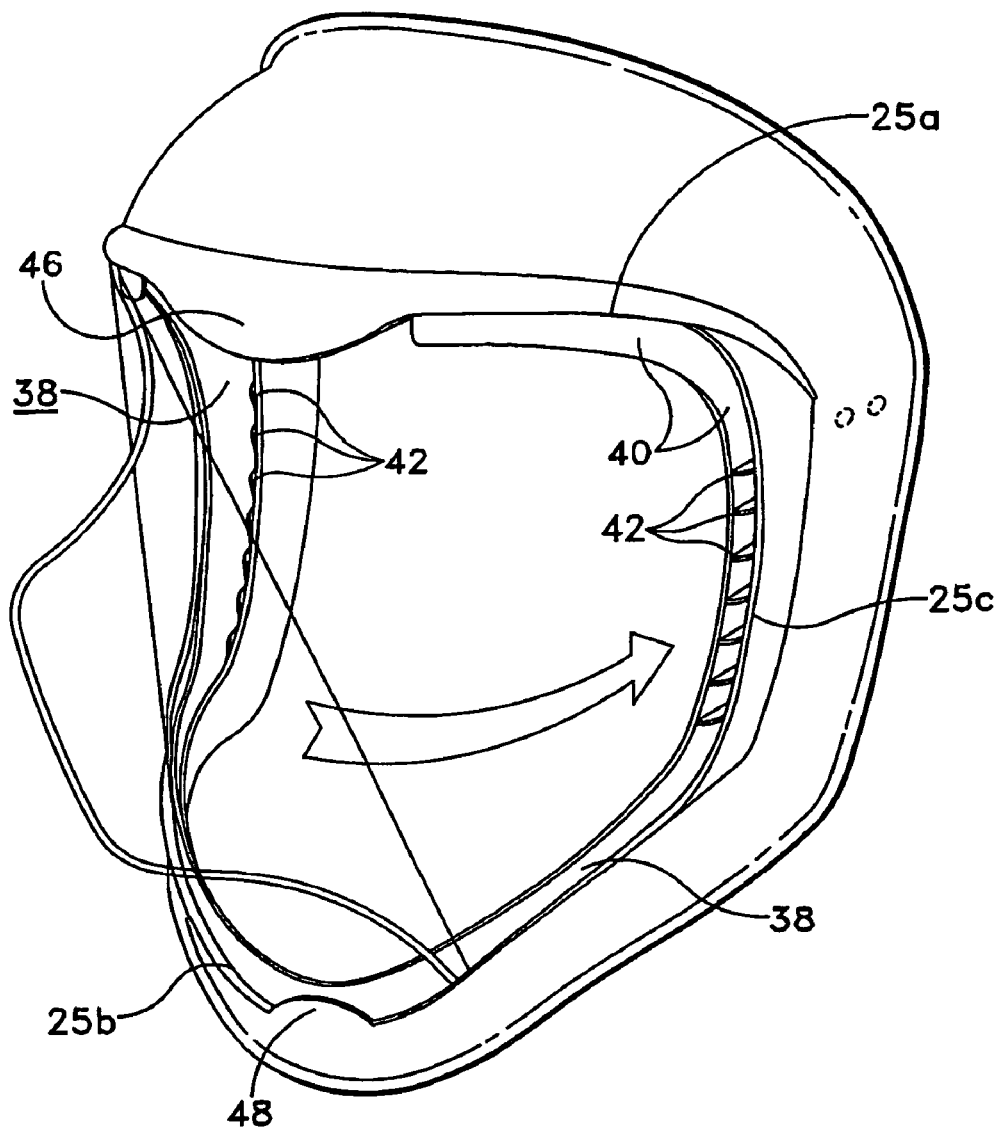
FIG. 4A is a perspective view of the face shield of FIG. 1 showing insertion of the protective element within the frame.
Figure 4B:
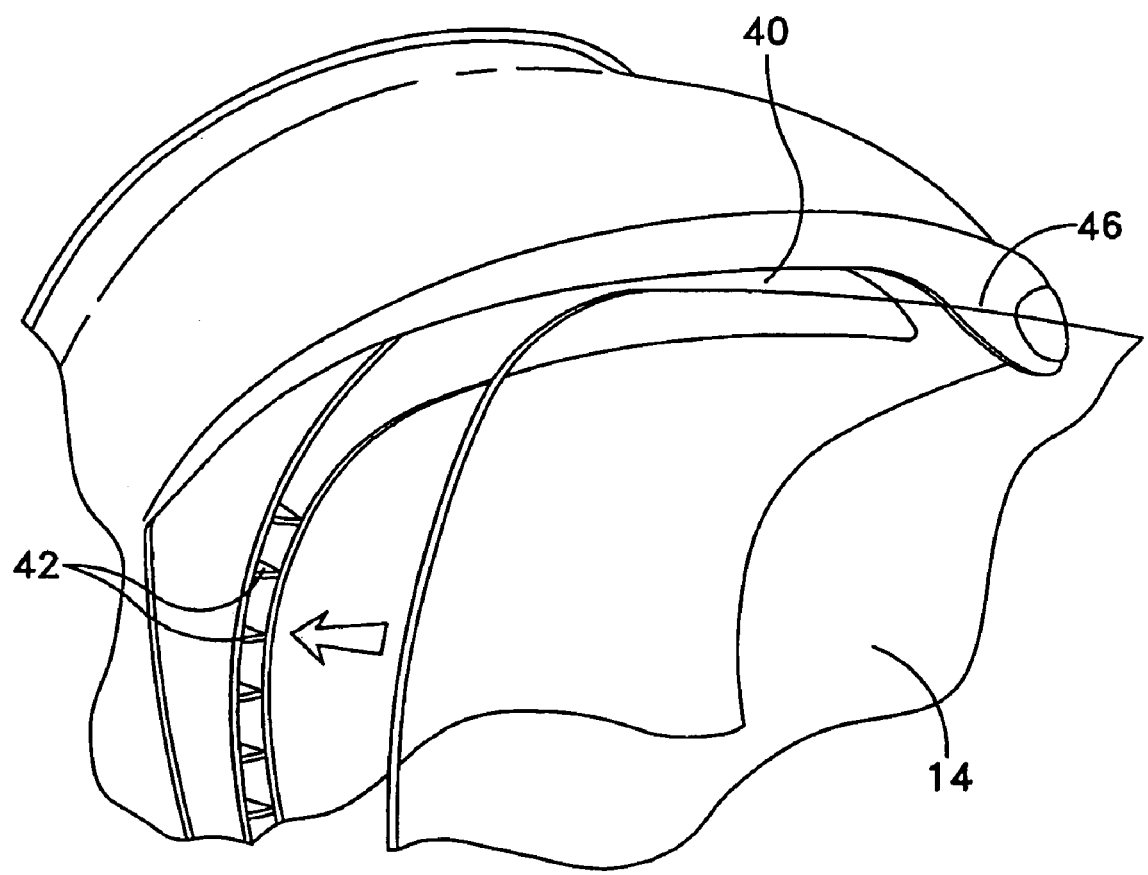
FIG. 4B is a partially enlarged view of the face shield of FIG. 4A showing insertion of the protective element within the right side of the frame.
Figure 5:
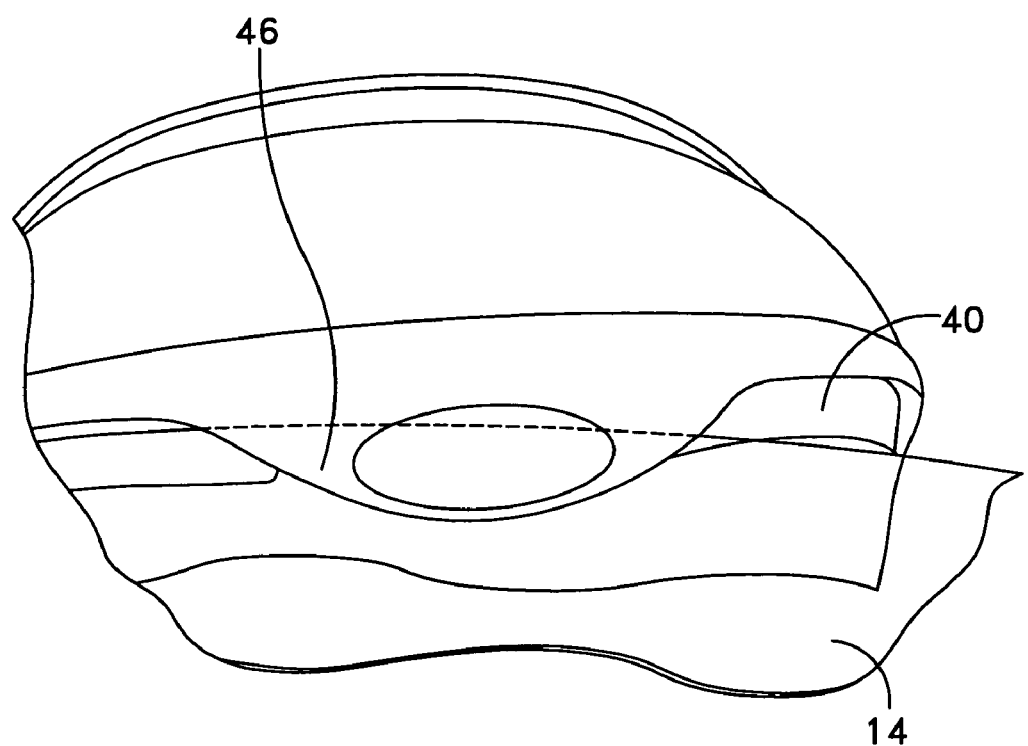
FIG. 5 is a partially enlarged view of the face shield of FIG. 1 showing insertion of the protective element within the top of the frame.
Figure 6:
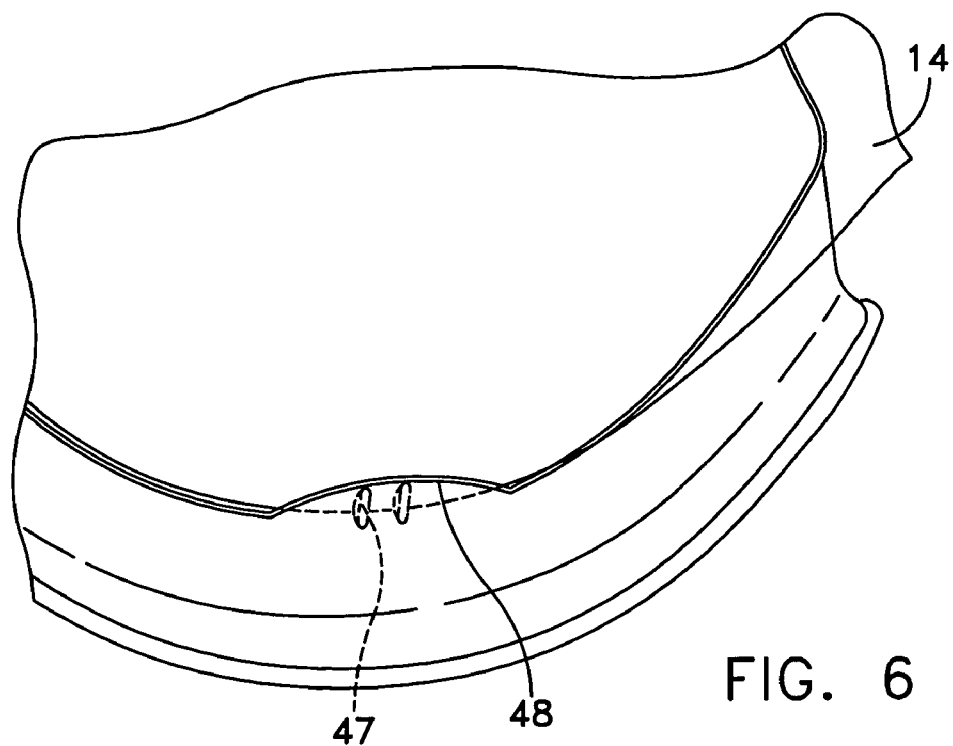
FIG. 6 is a partially enlarged view of the face shield of FIG. 1 showing insertion of the protective element within the bottom of the frame.
Figure 7:
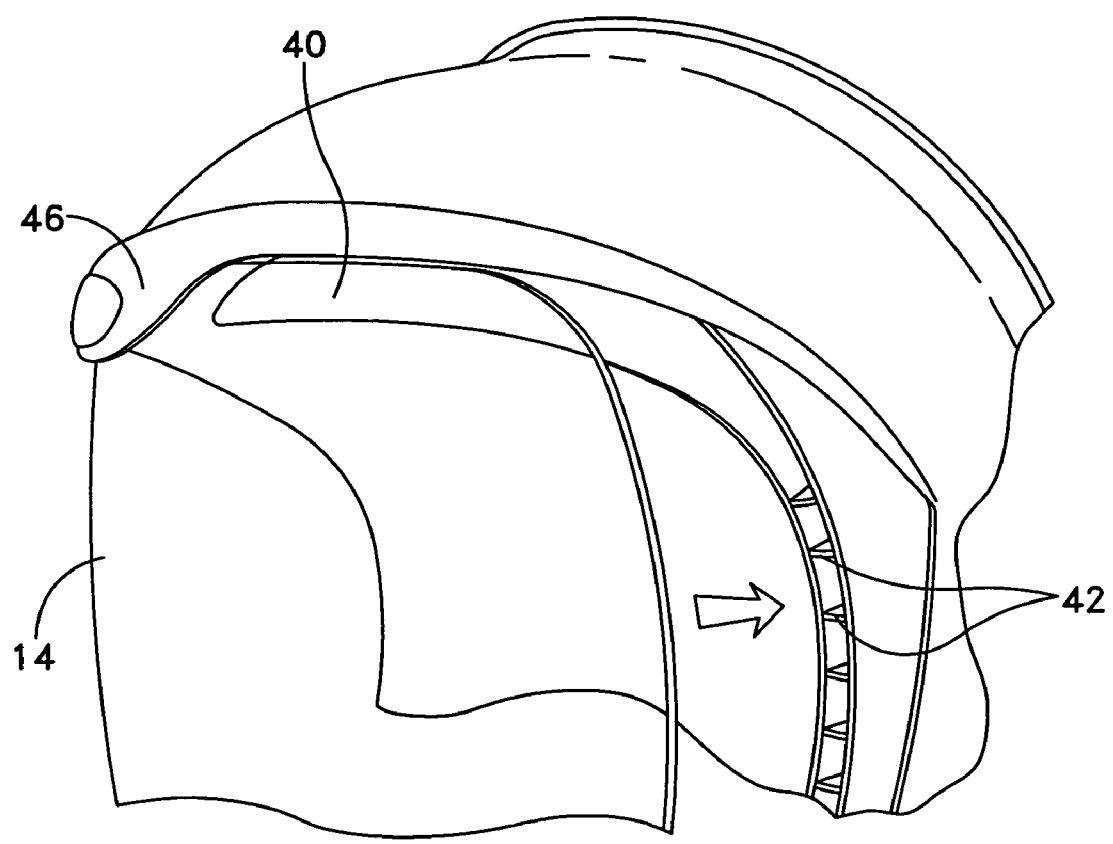
FIG. 7 is a partially enlarged view of the face shield of FIG. 1 showing insertion of the protective element within the left side of the frame.
Figure 8:
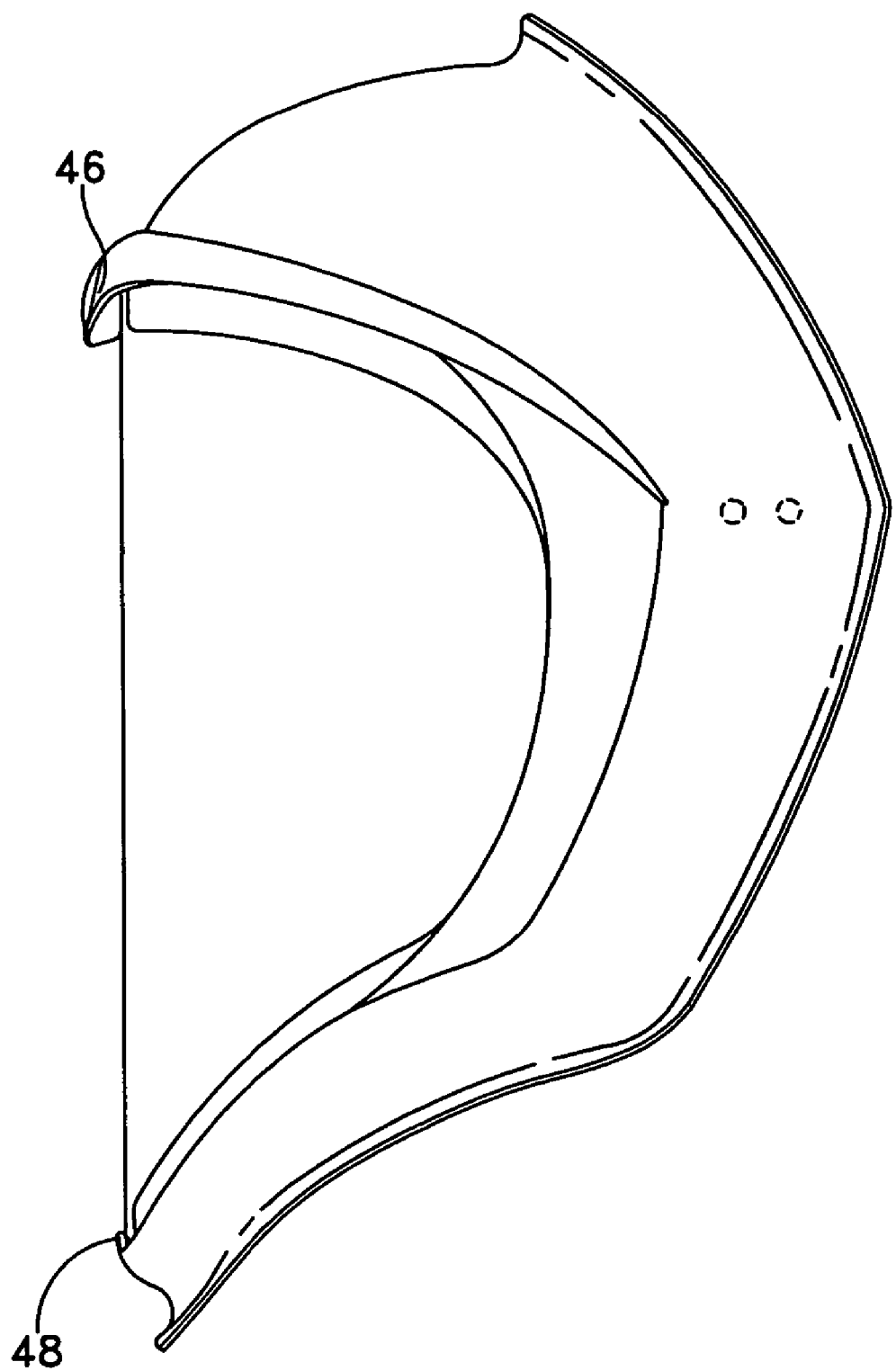
FIG. 8 is a left side view of the embodiment of FIG. 1.
Figure 9:
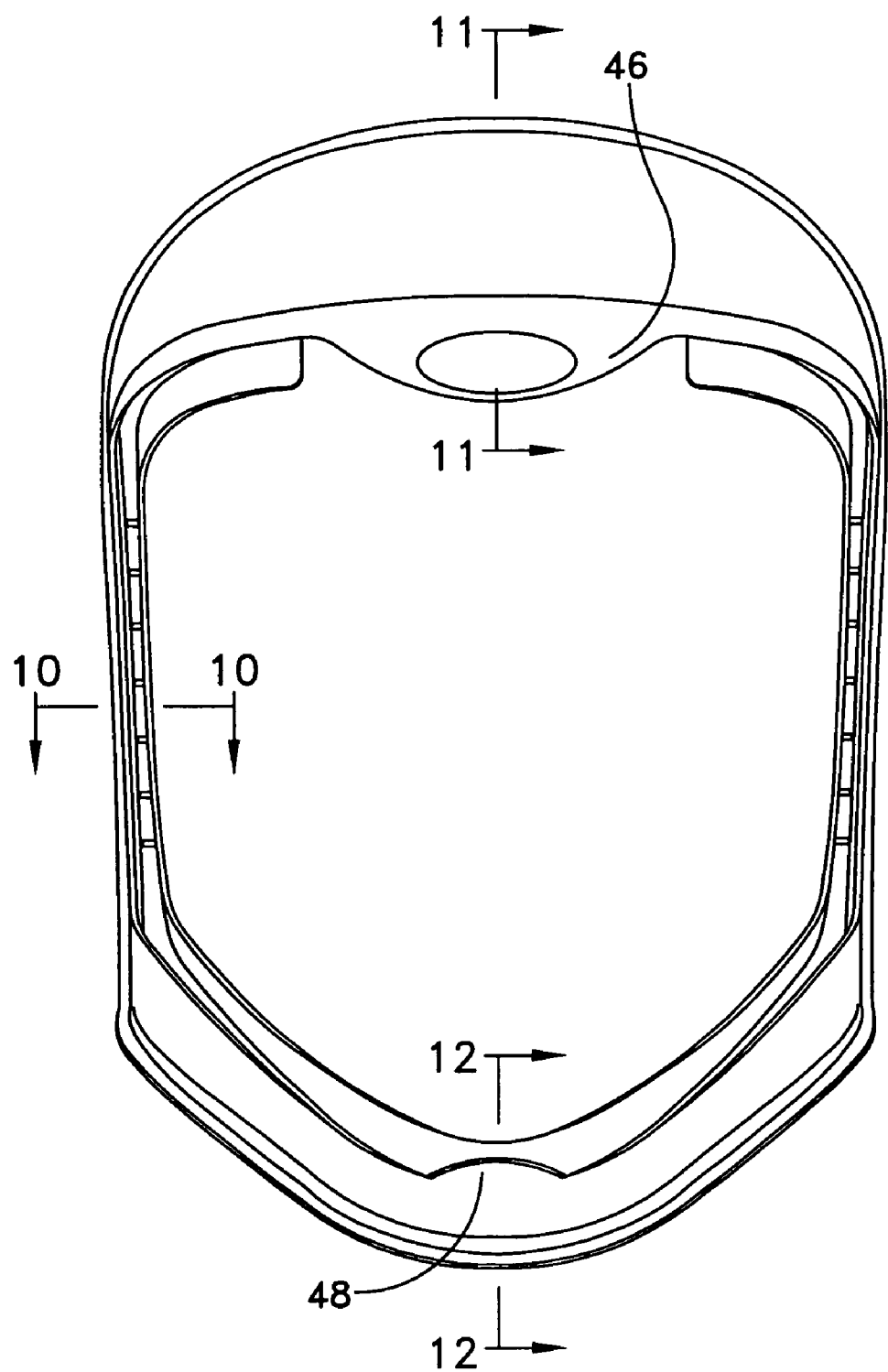
FIG. 9 is a front view of the embodiment of FIG. 1.

Referring now to FIG. 3, one embodiment of a protective element 14 is illustrated. In this embodiment the protective element is a lens 15, the lens preferably being substantially planar (i.e. flat) in the uninstalled position. The lens 15 is preferably injection molded into a sheet made of, for example, polycarbonate, acrylic, polyester, or any other of a variety of materials that are well known in the art. Alternately, the lens may not be flat in the uninstalled configuration and may be molded into a spherical or other rounded shape (not shown). The lens 15 may also be coated with a variety of chemical coatings, depending upon the particular application. For example, the lens may include an anti-fog coating, a reflective coating, may have a coating applied to improve the chemical and/or scratch resistance of the lens, or any other coating as is well known in the art. The lens is preferably shaped and sized to fit into the shape and size opening provided in the frame. In the present embodiment, the lens includes a slightly arcuate upper edge 30, side edges 32, which curve slightly inward from the ends 31a, 31b of the upper edge, and a lower edge 34 that defines a semicircular protrusion 36. Alternatively, a variety of shaped lenses (or protective elements) may be utilized, depending upon the shape of the corresponding opening, as described above. The lens is sufficiently flexible so that it curves without fracturing when placed within the opening of the face shield frame 12.

Figure 10:
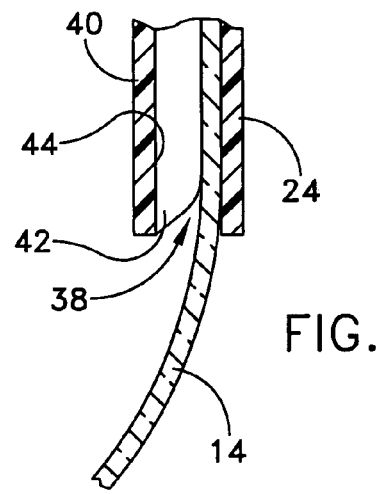
FIG. 10 is a cross-sectional view taken along lines 10—10 of FIG. 9.
Figure 11:
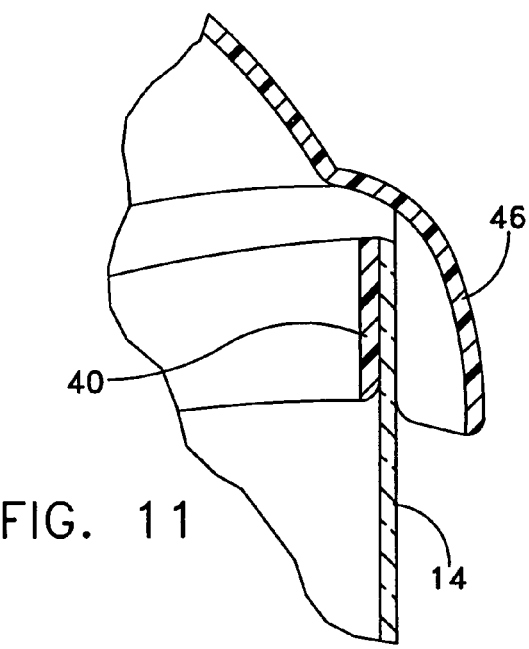
FIG. 11 is a cross-sectional view taken along lines 11—11 of FIG. 9.
Figure 12:
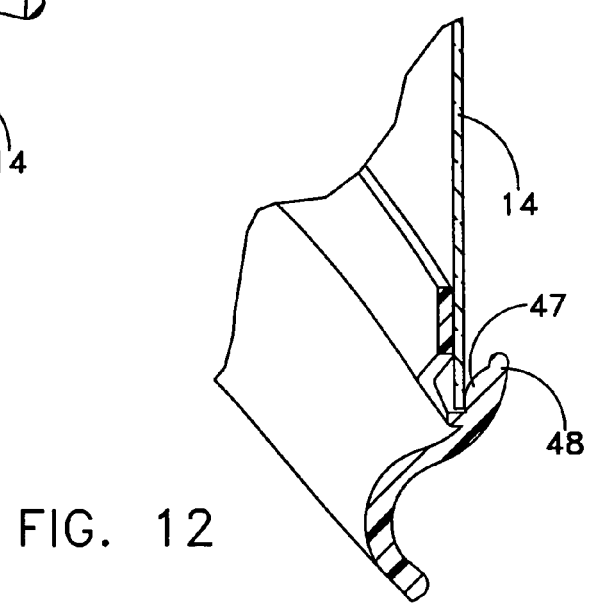
FIG. 12 is a cross-sectional view taken along lines 12—12 of FIG. 9.
Figure 13:
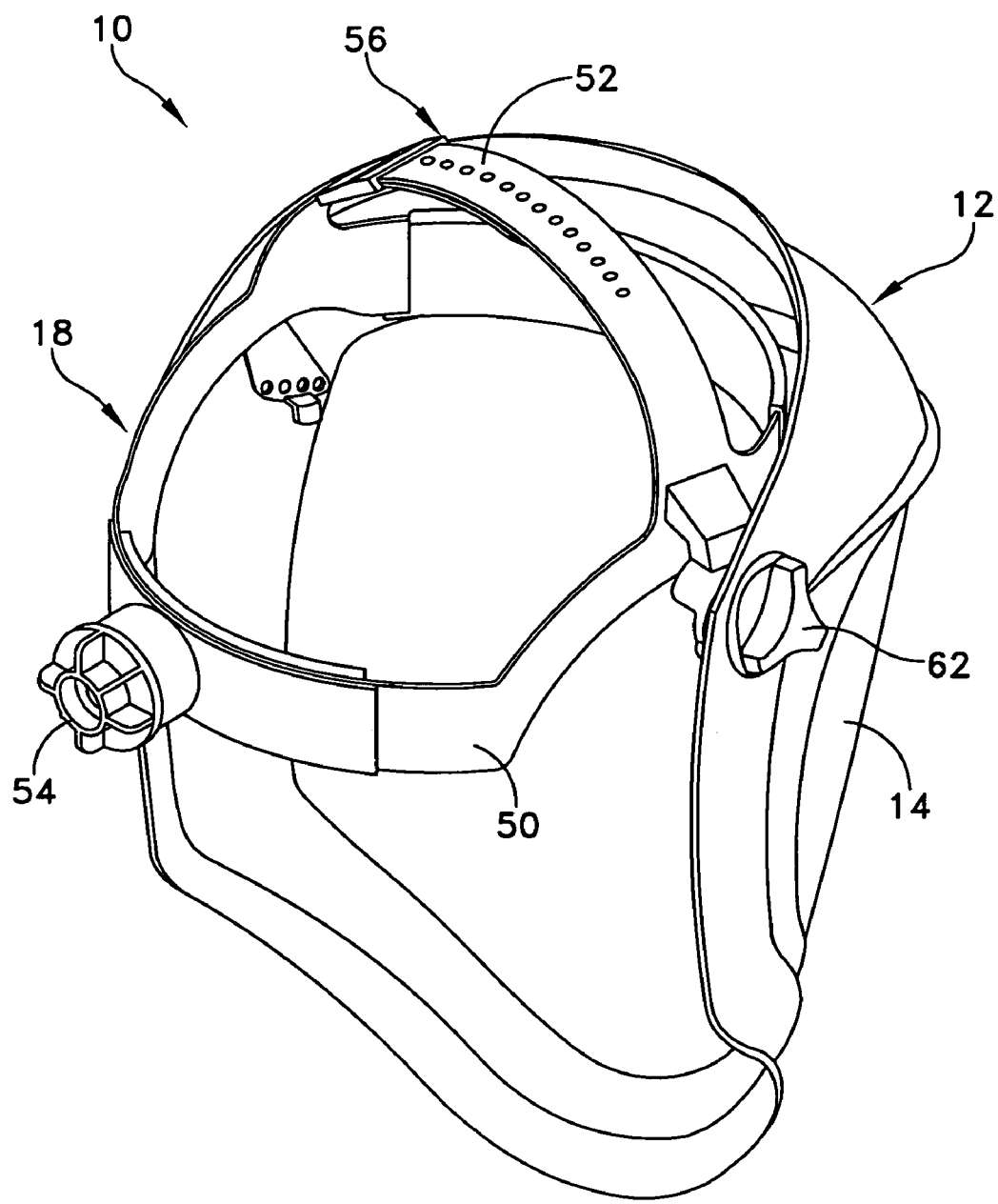
FIG. 13 is a rear perspective view of the face shield assembly of FIG. 1 mounted to a support structure.

Protective element 14 is removably secured within the frame by a groove or channel 38 that is preferably formed between the inner edges 25a,b,c, of the top, bottom and side portions and a lip 40. As best shown in FIG. 10, the channel 38 is formed between the inner edges 25a–c of the frame 12 and the lip 40, and is sized to receive the edges of the protective element 14. In order to more securely fit the protective element into the channel, a plurality of fingers or ridges 42 supported on an inner surface 44 of the lip 40 are preferably provided (See FIG. 7). The ridges 42 also aid in the manufacturing process of the shell by making the lip more rigid. Any suitable number of ridges may be provided, as desired. The lip 40 and ridges 42 may also be formed as a single, unitary piece with the remaining portion of the frame. Alternately, the pieces may be formed as separate members and joined in any manner, as known to those of skill in the art.

In addition to channel 38, an upper detent 46 and a lower detent 48 are also preferably provided. The upper and lower detents may be approximately centered on the top inner edge 25a and bottom inner edge 25b, respectively, of the frame. During use, the detents aid in placement and securing of the protective element 14 within the opening 16. Both the upper detent 46 and the lower detent 48 may include one or more ridges 47 to help secure the lens. Once the protective element 14 is secured within the channel 38 such that it covers the opening 16, a continuous outer surface is formed to protect the user's eyes and face from external hazards when the user wears the face shield assembly. As will be appreciated, because no fasteners are required to secure the protective element to the frame, the user may readily replace the protective element even with gloved hands. For example, if the lens is damaged it may be replaced, or if the user is changing applications a lens having different characteristics may be replaced for the existing lens. As will also be appreciated, because of the lack of fasteners, the inserting and removing the lens is simple and intuitive, even during the user's first replacement or insertion. This is true, at least in part, because once the edges are inserted within the channel the lens is self locating. In other words, there is no need for a specific alignment in order to place holes in a proper position with corresponding fasteners.

In order to secure the face shield frame and protective element in front of the user's face a head worn support structure 18 may be provided. In the present embodiment, the support structure may preferably be an adjustable strap style suspension system that fits onto the head of the user. Such an exemplary system is shown in greater detail in FIGS. 10–17. Alternatively, other types of support structures, for example hat style structures, may be utilized as is known in the art. The support structure 18 of the present embodiment preferably includes a first, adjustable strap 50 that extends around the circumference of the user's head during operation, and a second, adjustable strap 52 that extends over a top portion of the user's head during use. Such adjustable circumferential and top straps are known in the art and may be adjusted in any of a variety of known ways. For example, a knob 54 may be provided to adjust the size of the circumferential strap 50, while a buckle style adjustment 56 may be utilized to adjust the top strap 52, as shown in the present embodiment. The adjustability allows for a more comfortable, custom fit of the support structure on the head of the user.

Mounting members 58 are preferably provided to mount the support structure 18 on either side 24 of the inner surface of the frame 12. In the present embodiment, a fixed mounting element 59 having a plurality of mounting holes 61 is secured to the inner surface of either side of the frame. A corresponding, adjustable mounting element 63 is supported on either side of the support structure. In the present embodiment, the corresponding adjustable mounting elements are supported below the juncture of the adjustable straps 50, 52. A pair of mounting holes 60a, b may be provided on the adjustable mounting element 63 so that the frame may be selectively positioned relative to the user's face. A pair of knobs 62, each having a pin (not shown) are preferably utilized to support the adjustable mounting elements to the frame. If the pin is received through the distal mounting hole 60b (FIG. 16) a gap, "$G_D$", is formed between the user's face and an inner surface of the protective element 14. However, if the pin is received through the proximal mounting hole 60a (FIG. 17) a gap, "$G_P$", is formed between the user's face and an inner surface of the protective element 14. As will be appreciated the distance between the user's face and the inner surface of the protective element is greater for $G_D$ than for $G_P$. This allows the user to choose a specific spacing, as desired, during a particular operation. For example, if the user is wearing goggles with the face shield (as is common for many applications) then the user will probably choose to use the distal mounting hole 60b in order to create a greater gap and, hence, room for the goggles.

Figure 14:
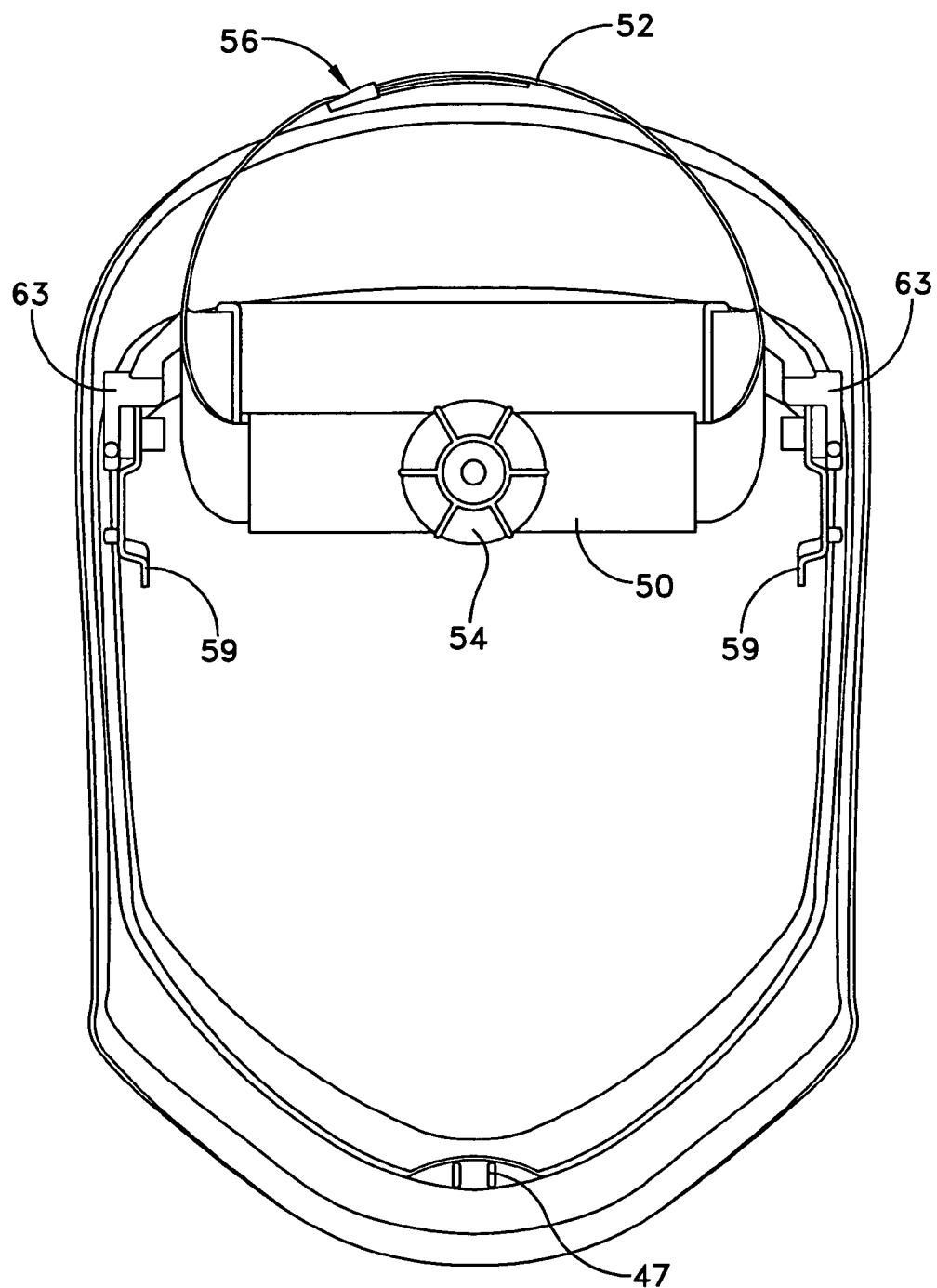
FIG. 14 is a rear view of the face shield assembly of FIG. 13.
Figure 15:
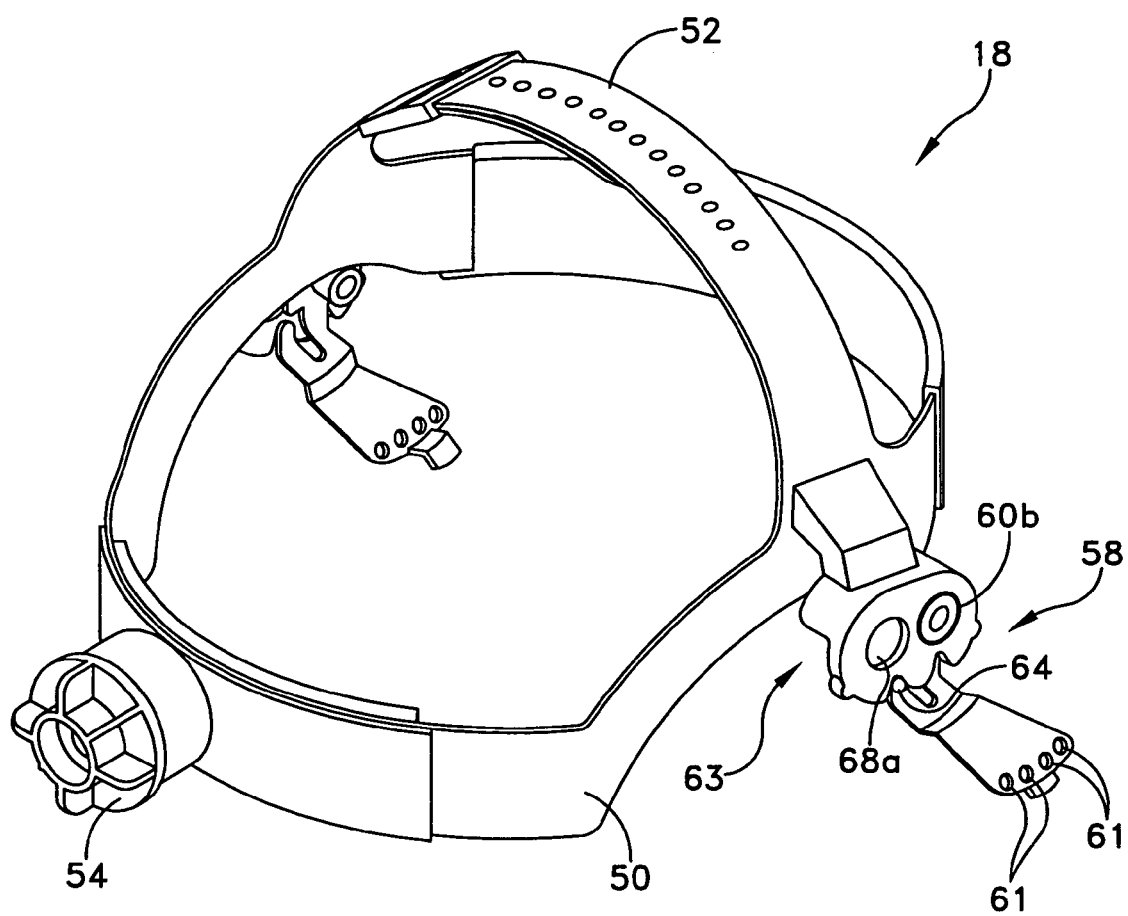
FIG. 15 is a perspective view of the support structure of FIG. 13 without the face shield.
Figure 16:
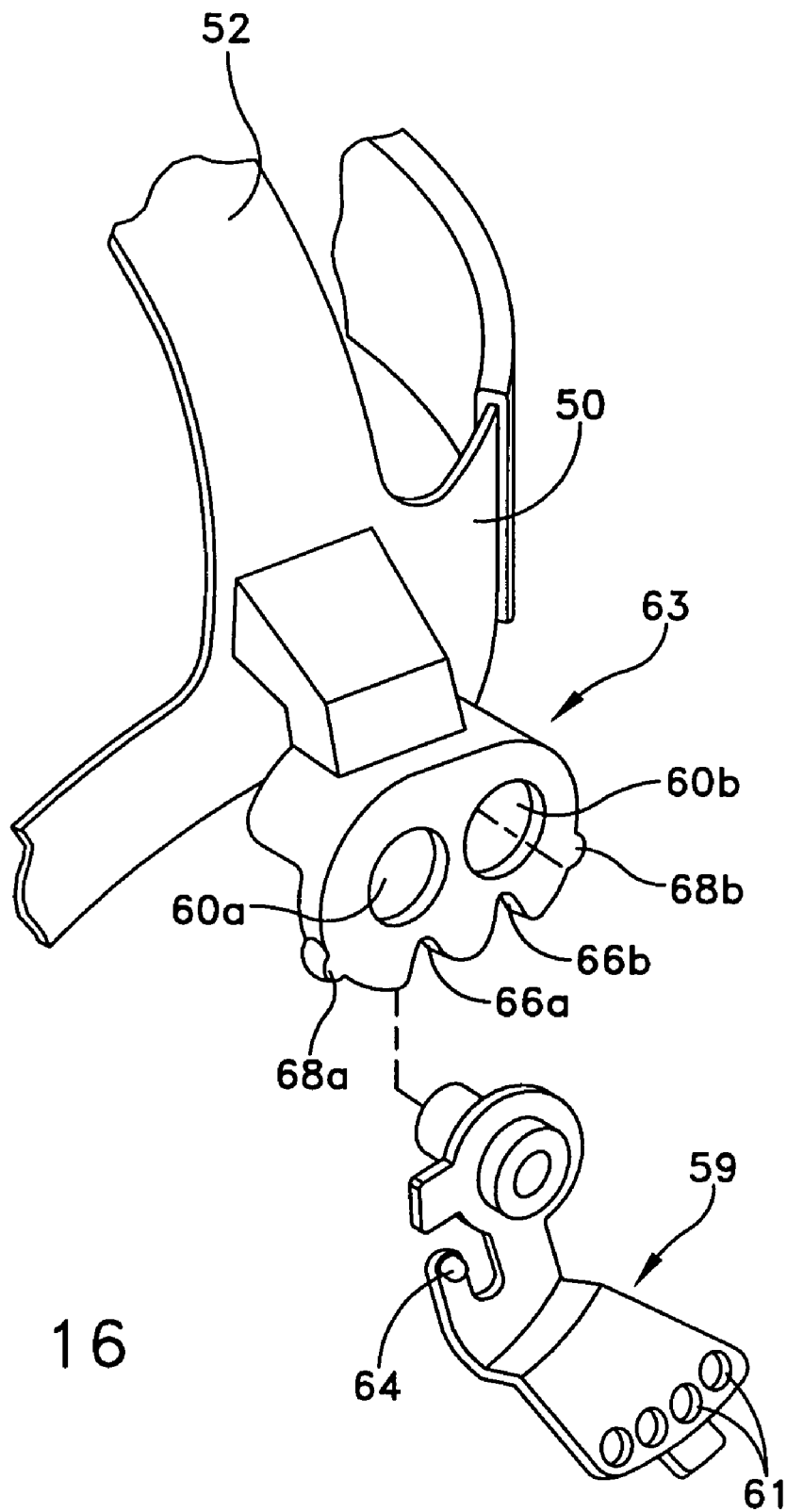
FIG. 16 is an enlarged, exploded view of the mounting device of the support structure of FIG. 13.
Figure 17:
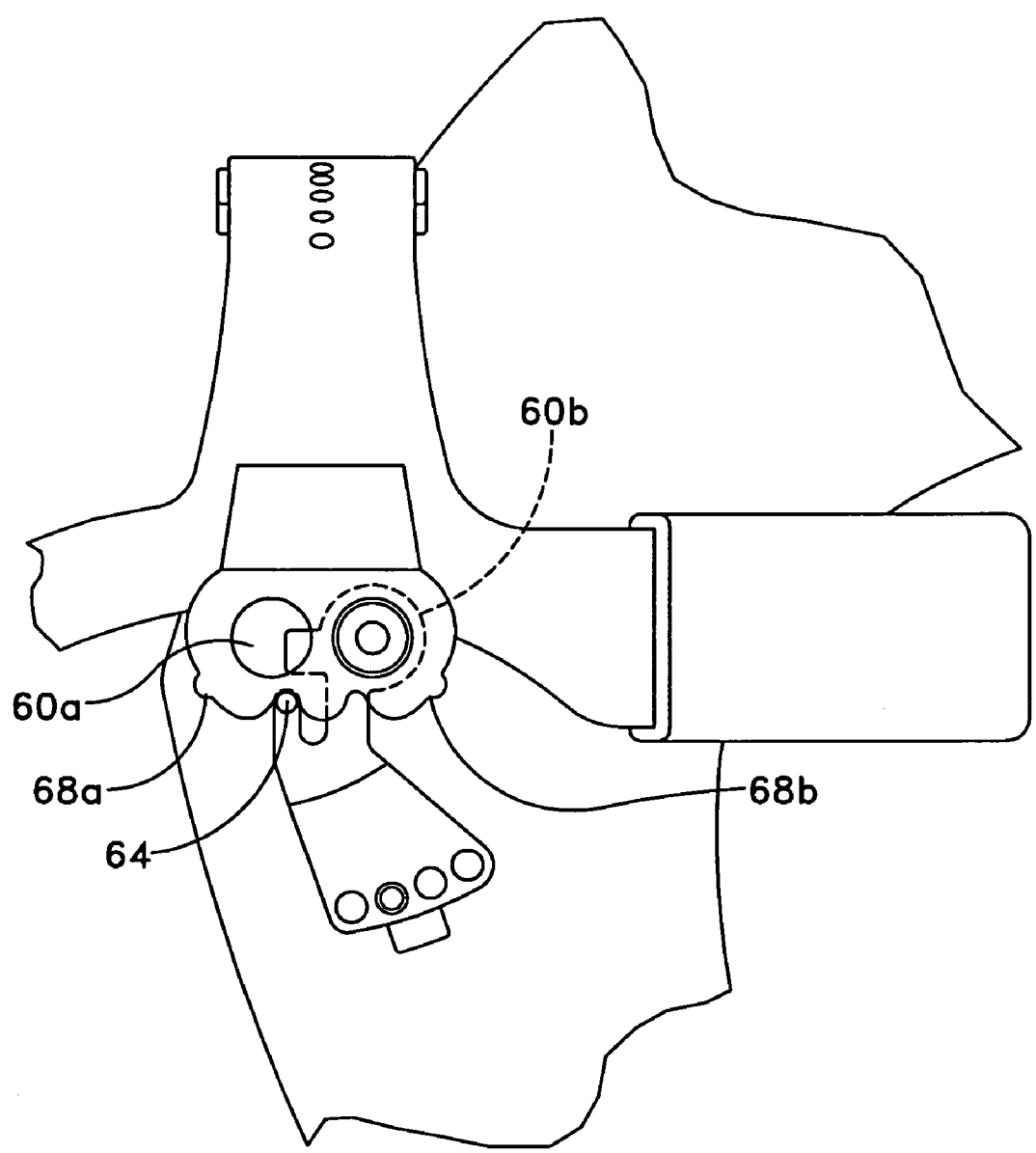
FIG. 17 is an enlarged, partial side view of the ratchet mechanism for the support structure of FIG. 13 in the first or lowered position.
Figure 18:
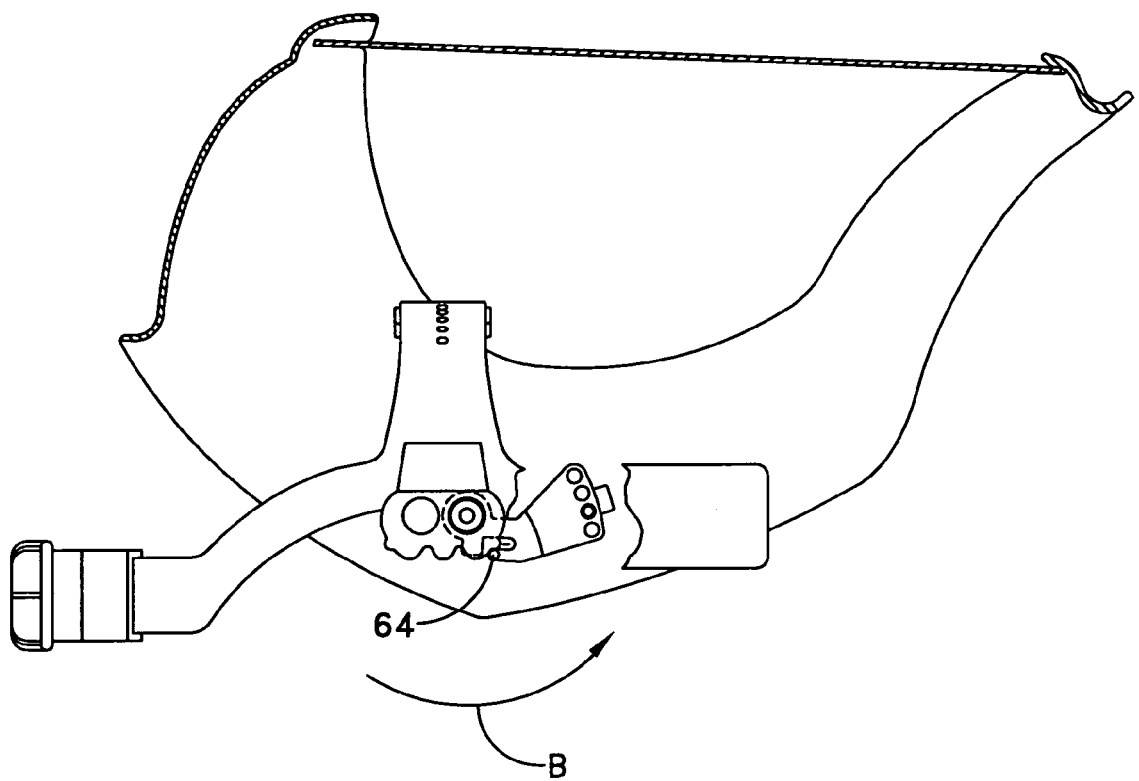
FIG. 18 is a side view of the ratchet mechanism for the support structure of FIG. 13 in the second or upper position.

In addition to being able to create an adjustable gap, the mounting members 58 also preferably include a pin 64 that is selectively engageable with at least two notches 66a, 66b formed in the mounting member in order to restrain the face shield in either the upper or lower positions. In the present embodiment, the pin is supported on the fixed mounting element and the at least two notches are formed in the adjustable mounting element, although the reverse configuration may also be utilized. A pair of stops 68a, 68b may also be provided in order to limit the movement of the face shield during use. For example, as shown in FIG. 14, the face shield is supported on the support structure by the distal mounting hole 60b and is in the lowered position, i.e. is covering the face of the user. In such a case, the pin 64 is received within first notch 66a. In order to move the face shield into the upper position, the user would lift the face shield in the direction of arrow "B" (FIG. 15) thus moving the pin out of the first notch 66a and into engagement with stop 68b. If, however, the face shield is supported on the support structure by the proximal mounting hole 60a and is in the lowered position the pin 64 would be in engagement with stop 68a (FIG. 17). As the face shield is lifted into the upper position, the pin would move into the second notch 66b. In this manner, the face shield is supported in either the upper or lower position until moved by the user.

Use of the face shield of the present embodiment will be described with reference to the Figures.

In use, the straps of the support structure is adjusted to fit the head of the user. The user can then chose to engage either the distal or proximal mounting holes in order to position the lens relative to their face, as desired. The lens may then be inserted within the opening in the frame by first inserting a side edge of the lens into a corresponding portion in the frame channel, and likewise inserting the top and bottom edges of the lens into the corresponding portion of the frame channel. The lens is also preferably positioned such that the central portion of the upper edge of the lens is behind the upper detent of the frame and the central portion of the lower edge of the lens is behind a lower detent of the frame. Once inserted into the channel, a continuous surface if formed to cover the opening in the frame and protect the user against unwanted hazards. The user may then selectively raise and lower the face shield frame, as desired, with at least two notches and stops holding the frame in position and limiting movement of the shield.

The face shield assembly disclosed herein has few moving parts and fasteners making it both easy to use and lightweight. The lightweight configuration and adjustability also make it comfortable to wear over extended periods. In addition, the lens is easy to replace and provides good visibility. The face shield assembly may also be readily adapted for use with other safety equipment. For example, a detent or snap may be placed on the top of the frame for connection with a hood and/or respirator.

It will be understood that various modifications may be made to the embodiments disclosed herein. For example, it should be understood that a variety of materials may be utilized for both the frame and the protective element, that the frame and lens may have alternate shapes other than those shown, depending upon the particular application, and that the frame need not be made as a unitary member. In addition, the frame and lens may be mounted to a variety of support structures. Therefore, the above description should not be construed as limiting, but merely as exemplifications of preferred embodiments. Those skilled in the art will envision other modifications within the scope, spirit and intent of the invention.

We claim:

1. A face shield assembly comprising:
   a protective element including an edge;
   a frame including a top portion, a bottom portion and a side portion, the frame further including:
   a) an opening sized to fit the protective element, the opening defined by an upper inner edge, a lower inner edge, and side inner edges of the frame;
   b) a lip spaced from the upper, lower and side inner edges so as to form a channel constructed and arrange to receive a portion of the edge of the protective element; and
   a support structure constructed and arranged to support the frame and adapted to be worn by a user;
   wherein the support structure includes a fixed mounting member that cooperates with an adjustable mounting member, said fixed and adjustable mounting members being supported between an inner surface of each side portion of the frame and opposite sides of the support structure;
   wherein the mounting member further includes a pin that is selectively engageable with at least two notches in order to restrain the face shield in one of an upper or lower position.

2. The face shield assembly of claim 1, wherein the frame further comprises:
   c) an upper detent supported by the frame;
   d) a lower detent supported by the frame; and
   wherein the upper and lower detents aid in placement of the protective element.

3. The face shield assembly of claim 1, wherein the frame is formed as a single, unitary member.

4. The face shield assembly of claim 1, wherein the opening is sized such that the frame does not obstruct the peripheral vision of the user.

5. The face shield assembly of claim 1, wherein the protective element is a lens.

6. The face shield assembly of claim 5, wherein the lens has a continuous, planar surface.

7. The face shield assembly of claim 5, wherein the lens has a continuous outer edge.

8. The face shield assembly of claim 1, wherein the fixed mounting element is supported on the inner surface of each side portion of the frame, and the adjustable mounting element is supported on opposite sides of the support structure.

9. The face shield assembly of claim 8, wherein the mounting member further comprising a pair of mounting holes constructed and arranged to allow the user to adjust the spacing of the lens relative to the user's face.

10. A face shield assembly comprising:
a protective element including an edge;
a frame mountable to a support structure and including a top portion, a bottom portion and a side portion, the frame further including:
a) an opening sized to fit the protective element, the opening defined by an upper inner edge, a lower inner edge, and side inner edges of the frame;
b) a lip spaced from the upper, lower and side inner edges so as to form a channel constructed and arrange to receive a portion of the edge of the protective element;
c) an upper detent supported by the frame;
d) a lower detent supported by the frame; and
wherein the frame lacks fasteners to secure the protective element, and the channel supports the protective element such that the protective element is removably attached to the frame so as to protect a user's face
wherein the upper detent is supported on approximately the center of the upper inner edge of the frame, and the lower detent is supported on approximately the center of the lower inner edge of the frame.

11. A face shield assembly comprising:
a protective element including an edge;
a frame mountable to a support structure and including a top portion, a bottom portion and a side portion, the frame further including:
a) an opening sized to fit the protective element, the opening defined by an upper inner edge, a lower inner edge, and side inner edges of the frame;
b) a lip spaced from the upper, lower and side inner edges so as to form a channel constructed and arrange to receive a portion of the edge of the protective element;
c) an upper detent supported by the frame;
d) a lower detent supported by the frame; and
wherein the frame lacks fasteners to secure the protective element, and the channel supports the protective element such that the protective element is removably attached to the frame so as to protect a user's face
wherein the lip includes a plurality of spacedly disposed transverse ridges that project into the channel.

12. A face shield assembly comprising:
a protective element including an edge;
a frame mountable to a support structure and including a top portion, a bottom portion and a side portion, the frame further including:
a) an opening sized to fit the protective element, the opening defined by an upper inner edge, a lower inner edge, and side inner edges of the frame;
b) a lip spaced from the upper, lower and side inner edges so as to form a channel constructed and arrange to receive a portion of the edge of the protective element;
c) an upper detent supported by the frame;
d) a lower detent supported by the frame; and
wherein the frame lacks fasteners to secure the protective element, and the channel supports the protective element such that the protective element is removably attached to the frame so as to Protect a user's face
further comprising a support structure constructed and arranged to support the frame and adapted be worn by a user
wherein the support structure includes a mounting member comprising a fixed mounting element supported on an inner surface of each side portion of the frame, and a corresponding, adjustable mounting element supported on opposite sides of the support structure
wherein the mounting member includes a pin that is selectively engageable with at least two notches in order to restrain the face shield in one of an upper or lower position.

13. The face shield assembly of claim 12, wherein the pin is supported on the fixed mounting element and the at least two notches are formed in the adjustable mounting element.

14. The face shield assembly of claim 12, further comprising a pair of stops for limiting movement of the face shield frame.

15. A face shield assembly comprising:
a protective element including a continuous outer edge;
a frame constructed and arranged as a single, unitary member, the frame including a top portion, a bottom portion and a side portion, the frame further including:
a) an opening sized to fit the protective element, the opening defined by an upper inner edge, a lower inner edge, and side inner edges of the frame;
b) means to receive a portion of the edge of the protective element;
a support structure constructed and arranged to support the frame and adapted to be worn by a user; and
an adjusting knob;
wherein the support structure includes a mounting member comprising a fixed mounting element secured to an inner surface of each side portion of the frame, and a corresponding, adjustable mounting element secured to an outer surface on opposite sides of the support structure;
wherein the adjustable mounting element further comprises at least a pair of mounting holes selectively engageable with at least said adjusting knob and constructed and arranged to allow the user to adjust the spacing of the protective element relative to the user's face.

16. The face shield assembly of claim 15, wherein the protective element comprises lens having a continuous surface.

17. The face shield assembly of claim 15, wherein the frame further comprises:
c) an upper detent supported by the frame;
d) a lower detent supported by the frame; and
wherein the upper and lower detents aid in placement of the lens.

18. The face shield assembly of claim 15, further comprising a lip spaced from the upper, lower and side inner edges so as to form the channel.

19. The face shield assembly of claim 18, wherein the lip includes one or more ridges that project into the channel to aid in securing the lens.

20. The face shield assembly of claim 15, wherein the opening extends from an approximate center line of the frame and is sized so that the frame does not obstruct the peripheral vision of the user.

21. The face shield assembly of claim 15 wherein the fixed mounting element has a boss that is engageable with either of said mounting holes and that receives a pin means of said adjustable knob.

22. The face shield assembly of claim 21 wherein said adjustable mounting element further includes at least two notches that are selectively engageable in order to restrain the face shield in one of an upper or lower position.

23. A face shield assembly comprising:
a protective element including a continuous outer edge;
a frame constructed and arranged as a single, unitary member, the frame including a top portion, a bottom portion and a side portion, the frame further including:
a) an opening sized to fit the lens, the opening defined by an upper inner edge, a lower inner edge, and side inner edges of the frame;
b) means to receive a portion of the edge of the protective element;
wherein the frame lacks fasteners to secure the protective element, and the frame supports the protective element such that the protective element is removably attached to the frame so as to protect a user's face;
a support structure constructed and arranged to support the frame and adapted to be worn by a user; and
a single adjusting knob;
wherein the support structure includes a mounting member comprising a fixed mounting element secured to an inner surface of each side portion of the frame, a corresponding, adjustable mounting element secured to an outer surface on opposite sides of the support structure and means for selectively interconnecting the fixed and adjustable mounting elements via the adjusting knob including engageable notch and pin means for setting different relative positions between the frame and support structure.

24. The face shield assembly of claim 23, wherein said protective element comprises a lens.

25. The face shield assembly of claim 24, wherein the adjustable mounting element further comprises at least a pair of mounting holes selectively engageable with at least said adjusting knob and constructed and arranged to allow the user to adjust the spacing of the lens relative to the user's face.

* * * * *